United States Patent
Kamlowski et al.

(10) Patent No.: US 7,838,298 B2
(45) Date of Patent: Nov. 23, 2010

(54) METHOD AND APPARATUS FOR DETERMINING THE FAT OR OIL CONTENT OF A SAMPLE

(75) Inventors: Andreas Kamlowski, Karlsruhe (DE); Dieter Schmalbein, Marxzell-Burbach (DE); Arne Kasten, Karlsruhe (DE)

(73) Assignee: Bruker Biospin, GmbH, Rheinstetten (DE)

( * ) Notice: Subject to any disclaimer, the term of this patent is extended or adjusted under 35 U.S.C. 154(b) by 1379 days.

(21) Appl. No.: 11/252,223

(22) Filed: Oct. 17, 2005

(65) Prior Publication Data
US 2007/0010021 A1 Jan. 11, 2007

(30) Foreign Application Priority Data
Oct. 19, 2004 (DE) ........................ 10 2004 050 737

(51) Int. Cl.
G01N 31/00 (2006.01)
G01N 33/06 (2006.01)
G01N 33/92 (2006.01)
G01V 3/00 (2006.01)

(52) U.S. Cl. ............................ 436/60; 436/71; 436/23; 324/307

(58) Field of Classification Search ................ 436/23, 436/60; 356/51; 324/307; 73/76; 374/14; 25/56
See application file for complete search history.

(56) References Cited

U.S. PATENT DOCUMENTS

| | | | |
|---|---|---|---|
| 5,284,144 A | | 2/1994 | Delannoy et al. |
| 6,548,303 B2 * | | 4/2003 | Collins et al. ................ 436/23 |
| 6,548,304 B2 * | | 4/2003 | Collins ........................ 436/23 |
| 6,787,362 B2 * | | 9/2004 | Collins et al. ................ 436/60 |
| 7,102,354 B2 * | | 9/2006 | Ardenkjaer-Larsen et al. .................... 324/321 |
| 7,220,591 B2 * | | 5/2007 | Collins et al. ................ 436/60 |
| 2002/0119575 A1 * | | 8/2002 | Collins ........................ 436/60 |
| 2004/0049108 A1 * | | 3/2004 | Ardenkjaer-Larsen et al. ... 600/412 |

FOREIGN PATENT DOCUMENTS

DE 41 33 643 C1 10/1991
GB 2 261 072 A 9/1992

OTHER PUBLICATIONS

Online article/definition, "Liquid Nitrogen," 2010.*
Poole, Charles P., Jr., "Electron Spin Resonance", John Wiley & Sons, Inc., 1983, pp. 654-659.

* cited by examiner

*Primary Examiner*—Jill Warden
*Assistant Examiner*—Bryan T Kilpatrick
(74) *Attorney, Agent, or Firm*—Law Offices of Paul E Kudirka

(57) ABSTRACT

A method and an apparatus serve the purpose of determining the fat or oil content of a sample. The sample is dried under the action of a microwave field and is examined under the action of a radio-frequency signal and of a constant magnetic field by means of nuclear magnetic resonance. The sample is exposed to the microwave field, the radio-frequency signal and the magnetic field at the same measuring place in a common measuring chamber. The apparatus has a microwave source for drying the sample, a magnetic system for generating a nuclear magnetic resonance magnetic field in the sample, and a nuclear magnetic resonance measuring arrangement for irradiating radio-frequency signals into the sample and for receiving excited nuclear magnetic resonance signals from the sample. The microwave source, the magnetic system and the nuclear magnetic resonance measuring arrangement are connected to a common measuring chamber in which the sample is located.

11 Claims, 1 Drawing Sheet

METHOD AND APPARATUS FOR DETERMINING THE FAT OR OIL CONTENT OF A SAMPLE

CROSS REFERENCE TO RELATED APPLICATION

The present application claims priority of German patent application 10 2004 050 737.6 filed on Oct. 19, 2004.

BACKGROUND OF THE INVENTION

The invention relates to a method for determining the fat or oil content of a sample.

The invention further relates to an apparatus for determining the fat or oil content of a sample.

In order to be able to measure the fat or oil content of samples, in particular of foodstuffs, in a quick way, it is known to examine the sample by means of low-resolving, pulsed nuclear magnetic resonance (NMR), for example with a resolution of $10^{-5}$ in a constant magnetic field of 1 tesla field strength, something which corresponds to a nuclear magnetic resonant frequency of protons of the order of magnitude of 50 MHz. Specially designed NMR spectrometers are commercially available for this purpose, for example from the applicant under the type designation of "minispec".

In the case of samples which also have a considerable water content in addition to the fat or oil, such a measurement is, however, attended by the problem that the strong proton signal of the water disturbs the measurement of the fat or oil content. It has therefore already been proposed in DE 41 33 642 C1 to predry the sample in an oven, for example a microwave oven, or to remove the water content at least partially by means of chemical drying.

U.S. Pat. No. 6,548,303 B2 describes a method and an apparatus of the type already mentioned, in the case of which method and apparatus the sample is relieved of its water constituent by predrying in a microwave oven. The sample is firstly introduced into a separate microwave oven for this purpose. There, the sample is heated in a controlled fashion under the action of a microwave field with a frequency of 2.45 GHz and while being monitored by a sensor, and is thereby dried. The sample is located in this case on a balance arranged in the microwave oven such that the weight loss of the sample is measured as drying proceeds, and it is therefore also possible in addition to determine the water content. After termination of the drying operation, the sample is removed manually from the microwave oven and transferred into a separate NMR analyser in which the nuclear magnetic resonance measurement then takes place.

This known mode of procedure has the disadvantage that the sample must be handled in a complicated fashion. In order to enable this handling, the substance of the sample must firstly be applied to a tissue fragment of quartz or glass fibres which acts as a substrate. This tissue fragment is transparent to microwaves and free from proton signals in the NMR measuring range of interest here. Since, because of the fat or oil fractions, the sample material liquefies as it dries out, at least for the NMR measurement the sample substance applied to the tissue fragment must further be wrapped in a film which consists of polytetrafluoroethylene (PTFE). All these steps are clearly very complicated and time-consuming. Automated measurements on a multiplicity of samples are therefore impossible with the aid of this known mode of procedure.

SUMMARY OF THE INVENTION

By contrast, the invention is based on the object of developing a method and an apparatus of the type mentioned at the beginning to the effect that these disadvantages are avoided.

Another object is to achieve a considerable simplification of the measurement procedure which also enables automated measurements on a multiplicity of samples.

According to a first aspect of the invention, a method for determining at least one of a fat or an oil content of a sample is provided, comprising drying the sample under the action of a microwave field, examining the sample under the action of a radio-frequency signal and of a constant magnetic field by means of nuclear magnetic resonance, wherein the sample is exposed to the microwave field, the radio-frequency signal and the magnetic field at the same measuring place in a common measuring chamber.

According to another aspect of the invention, an apparatus for determining at least one of a fat content or an oil content of a sample is provided, comprising a microwave source for drying the sample, a magnetic system for generating a nuclear magnetic resonance magnetic field in the sample, a nuclear magnetic resonance measuring arrangement for irradiating radio-frequency signals into the sample and for receiving excited nuclear magnetic response signals from the sample, the microwave source, the magnetic system and the nuclear magnetic resonance measuring arrangement being connected to a common measuring chamber in which the sample is located.

Specifically, because the two operations of drying and NMR measurement occur at the same place, it is no longer necessary to handle the sample between these operations. Consequently, the need to apply the sample substance to a substrate and, above all, the need to package the sample substance together with the substrate are also eliminated. Rather, the sample need only be introduced into a customary sample vessel, for example a customary NMR sample tube or glass, at the measuring place in the measuring chamber, where drying and measurement are then carried out at the same place. This enables a quick change of sample and thus also automated measurements on a multiplicity of samples.

In a preferred refinement of the method according to the invention, the sample is exposed simultaneously to the microwave field, the radio-frequency signal and the magnetic field.

This measure has the advantage that the measurement of the fat and/or oil content can proceed in the shortest possible time because the NMR measurement already starts when the microwave field is still switched on, whereas on the other hand the water content has already sunk to a level which is no longer disturbing for the NMR measurement.

In a further preferred exemplary embodiment of the method according to the invention the sample is additionally weighed.

This measure, which is known per se, has the advantage that the water content of the sample can additionally be determined quantitatively. This holds in a further development of this variant in particular when the sample is weighed after the action of the microwave field.

In particularly preferred variants of the method according to the invention, the sample and the microwave field are moved closer to one another during the action of the microwave field.

According to a first variant, in this case the sample is preferably moved or rotated, specifically further preferably about an axis which runs substantially transverse to the direction of the NMR magnetic field.

According to a second preferred variant, the microwave field is moved. This can preferably be done by varying the spatial distribution of the microwave field temporally, for example by exposing the sample to a travelling microwave field or a microwave field of changing frequency, or by virtue of the fact that an element influencing the spatial distribution of the microwave field is moved in the microwave field.

All these measures have the advantage that inhomogeneities in the microwave field are evened out, or at least their effect is diminished. Specifically, when the microwave field is stationary in space, the locations of the maximum electric microwave field are likewise located at spatially fixed points such that the sample substance could then be overheated at these locations. By contrast, the locations of maximum electric microwave field strength travel when the spatial distribution of the microwave field is varied temporally.

In a preferred variant of the apparatus according to the invention, the microwave source is connected to a microwave transmitting arrangement and the nuclear magnetic resonance measuring arrangement is connected to a radio-frequency transmitting and receiving arrangement, and the sample is tightly surrounded by the microwave transmitting arrangement and the radio-frequency transmitting and receiving arrangement.

This measure has the advantage that the arrangements which serve to irradiate the microwave field and to irradiate and receive the nuclear magnetic resonance radio-frequency signal can be designed in a fashion optimally adapted to the respective sample and the measuring chamber.

The arrangements are preferably arranged in this case in an air gap of the magnetic system.

This measure has the advantage that it is possible to use conventional resistive or permanent magnetic systems having an air gap.

In a first preferred refinement of the apparatus according to the invention, the microwave transmitting arrangement is designed as a microwave delay line and the radio-frequency transmitting and receiving arrangement is preferably designed as a radio-frequency coil. In particular, the microwave delay line is designed as a helical line and is arranged coaxially inside the radio-frequency coil.

This measure has the advantage of producing a design which is of particularly compact construction.

This holds, in particular, when the microwave delay line and the radio-frequency coil are structurally united to form a single coil.

In a second preferred refinement of the apparatus according to the invention, the microwave source and the nuclear magnetic resonance measuring arrangement are connected to a common resonator in which both the microwave field and the radio-frequency signal can be propagated.

This measure has the advantage of producing a particularly simple design in which both signals, specifically the microwave signal and the radio-frequency signal, are propagated in the same apparatus.

This holds, in particular, when the resonator is designed as a loop-gap resonator and the loop-gap resonator has a lateral cylinder surface with an axial slot and two covers arranged radially at a distance from axial ends of the lateral cylinder surface, the slot being short-circuited by a plurality of capacitors and the lateral cylinder surface as well as the covers being electrically conductive at least at one surface.

Furthermore, it is also preferred in the case of the apparatus according to the invention when means are provided for the relative movement of the sample and the spatial distribution of the microwave field.

This measure also has the advantage that inhomogeneities in the microwave field are evened out, or at least their effect is diminished.

Finally, a further embodiment of an apparatus according to the invention is distinguished in that the sample is arranged on a balance in the measuring chamber.

This measure, which is known per se, also has the advantage that the water content of the sample can additionally be determined quantitatively.

Further advantages follow from the description and the attached drawing.

It is self-evident that the above-named features and those following which are still to be explained can be used not only in the respectively specified combination, but also in other combinations or on their own without departing from the scope of the present invention.

BRIEF DESCRIPTION OF THE DRAWINGS

Exemplary embodiments of the invention are illustrated in the drawing and explained in more detail in the following description. In the drawings.

DETAILED DESCRIPTION OF PREFERRED EMBODIMENTS

Figure 1:
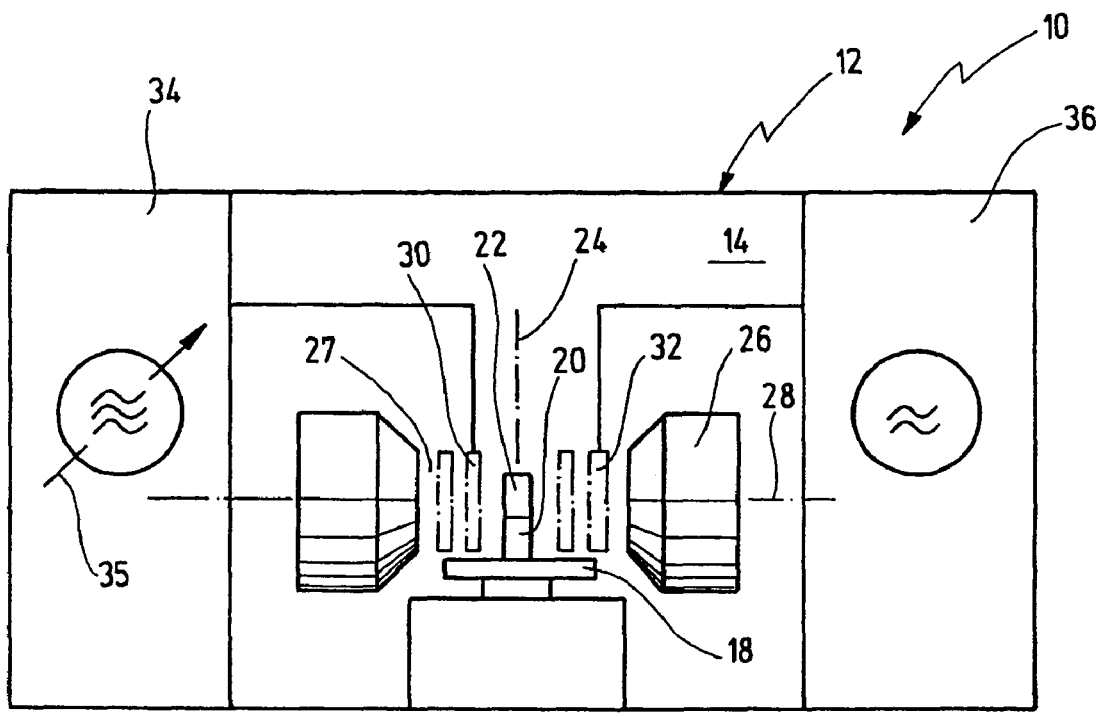
FIG. 1 shows a diagrammatic side view of an exemplary embodiment of an apparatus according to the invention.

An apparatus for measuring the fat or oil content of a sample is denoted as a whole by numeral 10 in FIG. 1. The apparatus 10 includes a measuring chamber 12 with an interior 14.

A balance 16 with a pan 18 is arranged in the interior 14. Located on the pan 18 is a sample 22, specifically expediently in a diagrammatically indicated sample vessel 24, for example a sample tube or glass, such as is used in nuclear magnetic resonance measurements. The sample in the sample tube defines a first axis 24, which is usually a vertical axis.

Figures 2, 3:
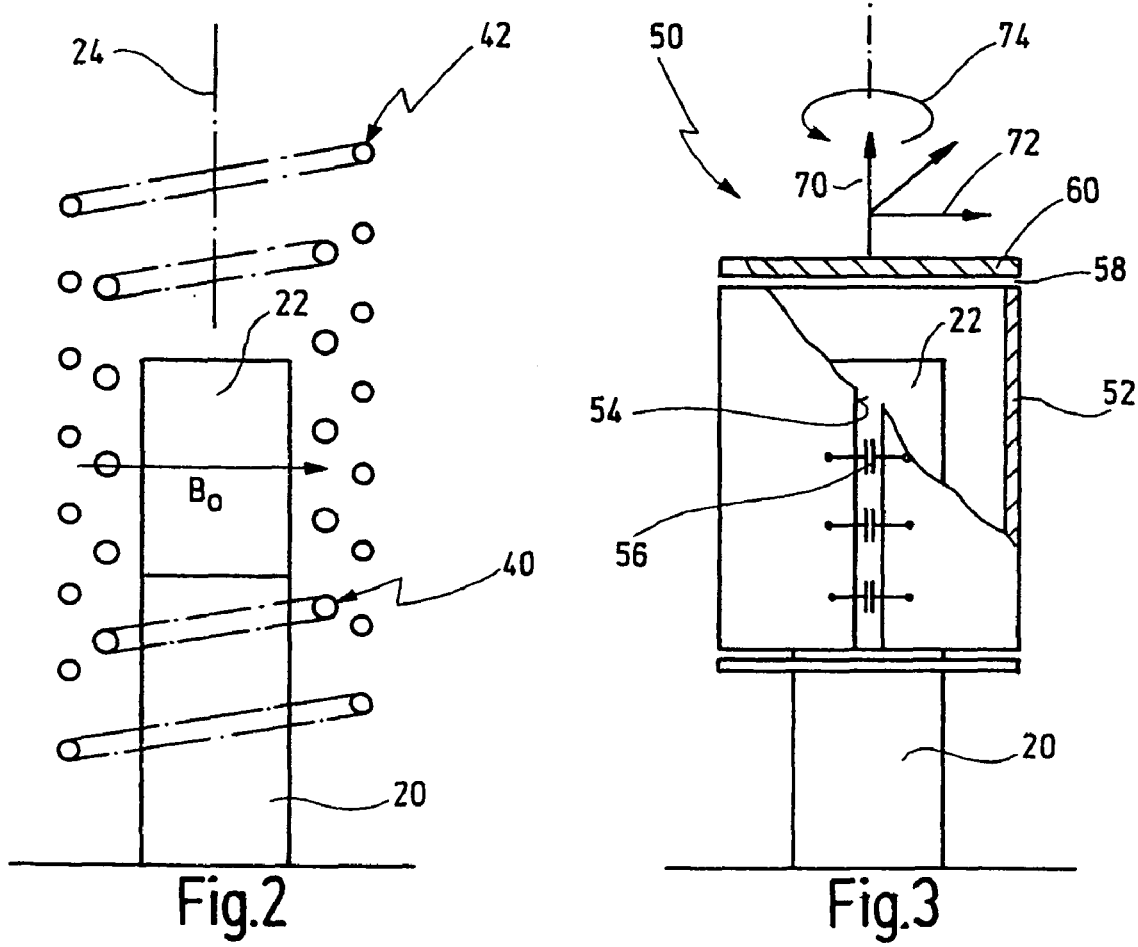
FIG. 2 shows on a greatly enlarged scale a transmitting and receiving arrangement such as can be used in the case of the exemplary embodiment in accordance with FIG. 1, with a microwave delay line.
FIG. 3 shows an illustration similar to FIG. 2, but for a transmitting and receiving arrangement with a loop-gap resonator.

The apparatus 10 further has a magnetic system 26. With regard to the homogeneity of the magnetic field produced by it, the magnetic system 26 need only satisfy average requirements, for example with a homogeneity of $10^{-5}$ over the volume of the sample 22. Such magnetic fields can be produced, for example, with the aid of electrically fed, resistive magnets in a U-shape whose poles are indicated diagrammatically in FIG. 1. An air gap 27 is located between the poles. As illustrated in FIG. 1, the magnetic system 26 can be located inside the measuring chamber 12, or else the measuring chamber is arranged as a whole in the air gap 27. Alternatively, it is also possible to use magnetic systems with permanent magnets. A second axis 28, which runs substantially transverse to the first axis 24, is defined by the magnetic system with the direction of the magnetic field $B_0$ produced by it (FIG. 2).

A microwave transmitting arrangement 30 and a radio-frequency transmitting and receiving arrangement 32 are located in the air gap 27. The microwave transmitting arrangement 30 is connected to a microwave source 34, and the radio-frequency transmitting and receiving arrangement 32 is connected to an NMR measuring arrangement 36. The frequency of the microwave source 34 can be set, as indicated by an arrow 35.

When "microwave" is talked of in the scope of the present application, it is to be understood as an electromagnetic wave such as is typically used to heat water-containing objects. This microwave is typically in the frequency range of a few GHz, for example in the so-called S-band in the range of 2.45 GHz. By contrast, "high frequency" is to be understood as an electromagnetic wave which is capable in conjunction with the field strength $B_0$ of the magnetic system 26 of exciting a nuclear magnetic resonance (NMR) of protons via the so-called gryomagnetic ratio. The high frequency is in the range of 50 MHz given a field strength of, for example, 1 Tesla.

In the exemplary embodiment illustrated in FIG. 1, the arrangements, 30, 32 tightly surround the sample 22 or the sample vessel 24. In this example, the microwave transmitting arrangement 30 is located inside, and the radio-frequency transmitting and receiving device 32 is located outside. However, this is in no way mandatory, because the relative positioning of these elements with respect to one another depends on the respective field distribution, in particular on the distribution of the electric microwave field effecting the heating of the sample 22, and of the magnetic radio-frequency field effecting the nuclear magnetic resonance in the sample 22. It is further to be ensured that no conductive elements for producing the respective other field may be present in the region of the electric component of one field, because this would otherwise lead to short circuits.

FIG. 2 shows a first variant of an arrangement for transmitting/receiving the microwave and radio-frequency signals. The microwave transmitting arrangement is designed in this case as microwave delay line 40, specifically as a helical line (helix). The delay line 40 extends along the first axis 24. Provided coaxially about the delay line 40 is a radio-frequency coil 42, specifically a solenoid coil. Such arrangements are known per se from electron nuclear double resonance measurements (ENDOR) (Poole, "Electron Spin Resonance", $2^{nd}$ edition, Dover Publications, Mineola, 1996, pages 654-657), but there serve the simultaneous excitation of electron resonances and nuclear magnetic resonances by the magnetic microwave field and the magnetic radio-frequency field in the same constant magnetic field.

A travelling field is produced in the delay line 40 and traverses the sample 22 in the direction of the first axis 24 such that the electric microwave field becomes effective at all locations of the sample 22 and therefore heats up said sample with sufficient uniformity that instances of local overheating are avoided. Electron resonances are therefore not excited because the frequency of the microwave field is not correlated with the constant field strength $B_0$ of the magnetic system 26 in accordance with the gyromagnetic ratio.

A pulsed nuclear magnetic resonance is excited in the sample 22 in the usual way by means of the radio-frequency coil 42 and, furthermore, the nuclear magnetic resonance signals of the sample 22 are received in the radio-frequency coil 42. It is also possible to use the microwave delay line 40 as radio-frequency coil such that a separate radio-frequency coil 40 is eliminated.

FIG. 3 shows a second variant of an arrangement for transmitting/receiving the microwave and radio-frequency signals. Here, the microwave transmitting arrangement and the radio-frequency transmitting and receiving arrangement are united in a common arrangement, specifically in a so-called loop-gap resonator 50.

The loop-gap resonator 50 essentially comprises a lateral cylinder surface 52 which is provided with a continuous axial slot 54 or gap. The slot 54 is short-circuited along its length with a plurality of capacitors 56. At its axial ends, the lateral cylinder surface 52 is sealed with a cover 60 in each case at a distance of an air gap 58. The lateral cylinder surface 52 and the covers 60 consist of an electrically conductive material or are coated with such a material.

The loop-gap resonator 50 constitutes a resonator for the radio-frequency signals. The covers 60 are non-existent for the radio-frequency signals because of the air gap 58.

For microwave signals, the loop-gap resonator 50 constitutes a conductive round waveguide, because the capacitors 56 act as short circuits for the microwave signals. The covers 60 terminate the round waveguides thus formed for the microwave signals as well in a fashion producing a resonator.

As a result, the microwave field in the loop-gap resonator 50 has a stationary field distribution such that a relative movement must be produced between the sample and the electric microwave field in order to avoid incidences of local overheating in the sample 22.

In a first variant, the loop-gap resonator 50 is provided with a flange 70 on which an actuator (not illustrated) acts. The actuator can move the loop-gap resonator 50 along Cartesian coordinates 72 or, for example, rotate it about the first axis 24, as indicated by an arrow 74. Alternatively, or in addition, a corresponding movement of the sample 22 is also possible.

In a second variant, the spatial field distribution is varied electrically, for example by sweeping the microwave frequency. However, this presupposes a satisfactorily broadband arrangement, or the use of high-order vibration modes. On the other hand, the field distribution can be varied by moving in the electric microwave field an electrically conductive or a dielectric element which influences the spatial distribution of the field.

What is claimed is:

1. An apparatus for determining at least one of a fat content and an oil content of a sample, comprising:
   a microwave source for drying said sample,
   a magnetic system for generating a nuclear magnetic resonance magnetic field in said sample,
   a nuclear magnetic resonance measuring arrangement for irradiating radio-frequency signals into said sample and for receiving excited nuclear magnetic response signals from said sample,
   said microwave source, said magnetic system and said nuclear magnetic resonance measuring arrangement being connected to a common measuring chamber in which said sample is located, said microwave source further being connected to a microwave transmitting arrangement and said nuclear magnetic resonance measuring arrangement being connected to a radiofrequency transmitting and receiving arrangement, said sample being tightly surrounded by said microwave transmitting arrangement and said nuclear magnetic resonance measuring arrangement, wherein said microwave transmitting arrangement and said nuclear magnetic resonance measuring arrangement are arranged in an air gap of said magnetic system.

2. The apparatus of claim 1, wherein said microwave transmitting arrangement is designed as a microwave delay line.

3. The apparatus of claim 1, wherein said radio-frequency transmitting and receiving arrangement is designed as a radio-frequency coil.

4. The apparatus of claim 2, wherein said radio-frequency transmitting and receiving arrangement is designed as a radio-frequency coil, and said microwave delay line and said radio-frequency coil are structurally united to form a single coil.

5. The apparatus of claim 2, wherein said radio-frequency transmitting and receiving arrangement is designed as a radio-frequency coil, and wherein said microwave delay line is designed as a helical line and is arranged coaxially inside said radio-frequency coil.

6. The apparatus of claim 1, wherein said microwave source and said nuclear magnetic resonance measuring arrangement are connected to a common resonator in which both said microwave field and said radio-frequency signal can be propagated.

7. The apparatus of claim 6, wherein said resonator is designed as a loop-gap resonator.

8. The apparatus of claim 7, wherein said loop-gap resonator has a lateral cylinder surface with an axial slot and two covers arranged radially at a distance from axial ends of said lateral cylinder surface, said slot being short-circuited by a plurality of capacitors, and said lateral cylinder surface as well as said covers being electrically conductive at least at one surface.

9. The apparatus of claim 1, further comprising means for moving said sample relative to a spatial distribution of said microwave field.

10. The apparatus of claim 1, wherein said sample is arranged on a balance in said measuring chamber.

11. The apparatus of claim 1 wherein said nuclear magnetic resonance measuring arrangement comprises a low resolution, pulsed nuclear magnetic resonance apparatus suitable for determining fat and oil content of a sample.

* * * * *